United States Patent [19]

Veltri et al.

[11] Patent Number: 5,102,909
[45] Date of Patent: Apr. 7, 1992

[54] PHARMACEUTICALLY USEFUL FURYL SUBSTITUTED DIHYDROXYETHYLBUTYROLACTONES

[75] Inventors: Robert W. Veltri, Gaithersburg, Md.; Gabor B. Fodor; Kawporn Sussangkarn, both of Morgantown, W. Va.

[73] Assignee: Theracel Corporation, Rockville, Md.

[21] Appl. No.: 535,771

[22] Filed: Jun. 11, 1990

Related U.S. Application Data

[63] Continuation-in-part of Ser. No. 225,964, Jul. 28, 1988, abandoned, which is a continuation-in-part of Ser. No. 89,525, Aug. 26, 1987, abandoned.

[51] Int. Cl.$^5$ ............... A61K 31/34; C07D 307/88

[52] U.S. Cl. ............... 514/470; 549/306; 549/476

[58] Field of Search ............... 549/306; 514/470

[56] References Cited

U.S. PATENT DOCUMENTS 4,620,014 10/1986 Szent-Gyorgyi et al. ........... 549/306

Primary Examiner—Jane T. Fan
Attorney, Agent, or Firm—Wyatt, Gerber, Burke and Badie

[57] ABSTRACT

The compounds 2-(5-methylthiomethyl-2-furyl)-2-hydroxy-3-keto-4-dihydroxyethylbutyrolactone and 2-(5-methoxymethyl-2-furyl)-2-furyl(-2-hydroxy-3-keto-4-dihydroxyethylbutyrolactone and pharmaceutical compositions containing them are useful to regulate the immune response in mammals.

12 Claims, No Drawings

PHARMACEUTICALLY USEFUL FURYL SUBSTITUTED DIHYDROXYETHYLBUTYROLACTONES

RELATED APPLICATIONS

This application is a continuation-in-part of application Ser. No. 225,964 filed July 28, 1988 now abandoned which is, in turn, a continuation-in part of application Ser. No. 89,525 filed Aug. 26, 1987.

BACKGROUND OF THE INVENTION

This application is concerned with the novel compound 2-(5-methylthiomethyl-2-furyl)-2-hydroxy-3-keto-4-dihydroxyethylbutyrolactone and the corresponding 5-methoxy-compound which for convenience will be referred to herein as MTMFBL and MMFBL. It is concerned also with pharmaceutical compositions containing either or both of these as the principal active ingredient or ingredients, and with methods of using the compounds for their physiological activity, especially to regulate the immune response in mammals.

The compounds which are the subject of the invention can be represented by the formula:

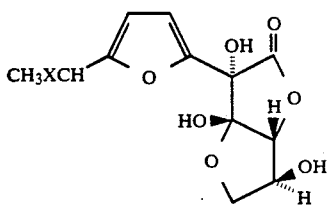

wherein X is sulfur or oxygen.

The compounds of the invention are useful as immunomodulating agents. They can be formulated with conventional pharmaceutical carriers for administration to animals and humans. The compound and compositions containing them show immunomodulatory activity, both immunostimulation and immunosuppressoon. As such they are useful for treatment of a wide variety of mammalian disorders which require control of the immune system. These include, for example, stimulation of the immune system following chemotherapy or radiation therapy. They are useful to stimulate the proliferation of helper cells in diseases such as measles, retroviruses (HTLV-III), and leprosy which are characterized by an undesirably high concentration of suppressor cells. They are also useful in the early stages of various infections to stimulate the production of interleukins, interferons, and other natural lymphokines.

Therapeutic agents useful to effect immunosuppression are extremely valuable. One such agent, cyclosporine is widely employed to prevent rejection in the case of organ transplants. The compounds of this invention have similar activity, and are also useful to inhibit the progress of autoimmune diseases such as multiple sclerosis, systemic lupus erythematosus, asthma, and rheumatoid arthritis.

The immune system is one of the primary defenses against disease causing microbes and other foreign proteins in higher animals. An immune response is mediated by the action of specific antibody proteins which react to specific antigens. Antigens are substances of fairly high molecular weight, often proteins, which are foreign to an individual's body. They are most frequently located on the outer surfaces of cells. Potential antigens can be found, for example, on pollen grains, tissue grafts, some tumor cell surfaces, animal parasites, viruses, and bacteria.

In humans, many potential antigens never pass the body's first two defense lines and therefore may not provide sufficient stimulation to the immune system. These two primary defense lines consist firstly of the skin, mucous membranes, tears, and stomach acid and secondly of specialized white blood cells, granulocytes and monocytes, and macrophages which may destroy pathogens and other potential antigens by phagocytosis, that is by engulfing and destroying the foreign material. These white blood cells and macrophages are called phagocytes. When pathogens or other foreign substances do pass the body's first two defense lines, the immune response begins.

There are two potential compartments of the immune defense system, humoral and cellular, both of which react to antigens. Humoral immunity is due to circulating antibodies which are found in the gamma globulin fraction of the plasma proteins. When plasma is centrifiged at high speed or chemically precipitated with ethanol by the Cohn procedure its component proteins separate by weight or charge into sections called fractions. Antibodies are usually found in the gamma globulin fraction whose components have a sedimentation constant of about 7–10 S. The IgG fraction has a molecular weight of approximately 156,000. Humoral immunity provides long term protection against bacterial and viral infections. Cellular immunity is partly due to direct lymphocyte interaction, or reactions with their products called lymphokines. This type of immunity is responsible for delayed allergic reactions, rejection of transplant of foreign tissue, and rejection of tumor cells. It is the major defense against infections due to viruses, fungi, parasites, and a few bacteria such as the tubercle bacillus and plays a key role in recovery from such infections.

Specialized white blood cells called lymphocytes are responsible for both humoral and cellular immunity. The lymphocyte precursors originate as hematopoietic tissue ontogenetically (prenatally) in the embryo before the appearance of bone. It is first evident in the yolk sac as "blood islands", small clusters of hematopoietic cells linked with the yolk blood vessels. These islands contain the multipotential hematopoietic cells termed stem cells. As the embryo develops, hemopoietic cells invaginate into the body stock and into the mesenchymal bed in the anterior ventral portion of the abdomen contigous with the stalk. The liver migrates into this same site of the body mesenchyme as an evagination from the gut epithelium, proliferates, and assumes the architecture of hepatic cords among hemopoietic cells. The liver thereby becomes a hemopoietic organ until close to parturition. About half way through gestation the bone cavities begin to demonstrate definite hematopoietic tissue. As mammals approach embryonic maturity hematopoiesis recedes in the liver and the bone marrow becomes the dominant hematopoietic organ.

Post-natally the lymphoid organs of the body house the immunologically competent lymphocytes which characterize the immune system. The bone marrow houses the stem cells (precursor of all myeloid and lymphoid cellular elements). Some of these stem cells migrate to one of the primary lymphoid organs of man and other mammals, the thymus. The thymus is a multilobed organ that lies high behind the sternum. Here, the stem cells proliferate and differentiate into mature T-lymphocytes which then enter the circulation and seed secondary lymphoid organs including the spleen, lymph nodes, tonsils, appendix, and Peyer's patches in the gut. The bone marrow also seeds the gut-associated lymphoid system, distributed along the gut, with pre-B cells. These cells then proliferate and differentiate under the influence of antigenic stimulation and migrate to the same secondary lymphoid organs described above. The T-cells and B-cells are structurally and functionally distinguishable through various biological, immunochemical and biochemical means.

Humoral immunity is mediated by the B-lymphocytes which have immunoglobulin receptors for particular antigens on their cell surfaces. They seem to be very specific and each type of B-lymphocyte reacts to only one antigen. When bacteria or viruses, for example, invade an organism, B-lymphocytes react to and combine with the antigens on the bacterial or viral surface and the lymphocyte is stimulated to divide. Its daughter cells differentiate into specialized cells called plasma cells. These cells produce and then secrete large quantities of antibodies into the general circulation. The antibodies are specific for the antigens which stimulated their production and react only with those antigens. Antibodies formed in response to antigens by the plasma cells may be functionally differentiated as cytophilic, that is they are capable of combining with cellular antigens and enhancing phagocytosis by monocytes, macrophages and polymorphonuclear granulocytes in the peripheral circulation. Such antibodies may also be cytotoxic and in combination with cellular antigens in the presence of complement may cause lysis. Other antibodies may in the presence of specific antigen-sensitized T-cells product antibody dependent cell lysis of tumor cells or virus infected cells. Antibodies produced to toxins or viruses may neutralize their toxicity or infectivity respectively by combining with the appropriate critical site for biological activity. Still other antibodies may be directed against the idiotypic determinant of an antibody molecule (the variable domain of the molecule), thereby being defined as an anti-idiotype or anti-antibodies (antibody 2) which are capable of regulating specific antibody synthesis or maintenance of antibody levels. In the latter cascade, antibody may be formed to the anti-idiotype generating a new antibody (antibody 3) with a specificity to the original antigen. The latter may be achieved without the immunized animal ever having experienced challenge with the original antigen. Such technology may be of value in modifying the course of autoimmune or malignant diseases.

Once a pathogen invades the body and the immune response begins, antibodies are made between 10–14 days later. This initial reaction is called the primary response or primary immunization. However, during that time, the pathogens have also been dividing and producing various disease symptoms. It may take days or weeks before enough antibodies are made to eliminate all the pathogens but once they disappear, the disease symptoms disappear as well. The lymphocytes, plasma cells, and antibodies remain and circulate in the blood so that if the same pathogens enter the body a second time, the B-memory lymphocytes react immediately and start antibody production. The response of these pre-sensitized lymphocytes is called the secondary response. The secondary response results in the production of higher levels of antibody than were currently circulating in the plasma. So many antibodies are produced so rapidly that the microbes are unable to establish themselves, divide, and cause disease under the latter circumstances.

Humoral immunity produced by the IgE isotype of immunoglobulin has as one of its efferent reactions immediate hypersensitivity due to the fact that a previously exposed organism can respond within minutes to an antigen, as in the case of hay fever. Another example of immediate hypersensitivity would be anaphylactic shock, an extreme allergic reaction that sometimes occurs when an individual is exposed to an antigen to which he has been sensitized. Sometimes, this humoral response to the antigen can result in death.

Humoral immunity can also be both naturally and artificially induced. In the case of active natural acquired immunity, an individual's B-lymphocytes continue to circulate and activate the production of antibodies after an infection. This active natural acquired immunity lasts for many years or even a lifetime. An infant receives antibodies from the colostrum, milk secreted by the mother, the first few days after birth, which provides immunity during the first year of its life. This is known as passive natural immunity since the infant is not involved in the actual production of the antibodies. Active artificial immunity is induced by injecting dead or weakened (attenuated) microbes or synthetic antigens into an individual. These antigens can still trigger B-lymphocytes to produce antibodies against the causative pathogen. When the individual is later exposed to the virulent microbe, he is already sensitized and immediately responds with a massive secondary (memory) production of antibodies. Active artificial immunity may last many years or permanently with booster shots. There is also a form of passive artificial immunity which provides protection for about one month. This temporary immunity is brought about by injecting antibodies obtained from another person or animal into an individual. It is usually only used in crisis situations and epidemics. Because the lymphocytes are by passed, they neither make antibodies nor "remember" the antigen, which accounts for the temporary effect of this method.

In cellular immunity, as contrasted to humoral immunity, circulating antibodies are not detectable. The T-lymphocytes which mediate this type of immunity are activated when they encounter antigens on cells from another individual, as in the case of transplants, tumors, bacterial, or parasites or viruses. Like B-lymphocytes, T-lymphocytes are specific and each type reacts with only one antigen. The T-lymphocytes in the peripheral circulation are divided into subpopulations with different effector functions in the immune response. The T-helper inducer subpopulation has a specific receptor for antigen and is responsible for augmentation of the production of specific antibodies to the antigen by B-cells. The T-helper inducer is identified in humans by a surface marker referred to as the T-4 antigen and can be detected with monoclonal antibodies. Another key T-lymphocyte subpopulation is the T-suppressor inducer (T-8 antigen surface marker) lymphocyte which regulates the magnitude of response of certain T- and B-cells to specific antigens. There are also T-cytotoxic (killer) cells which can bind directly to target tumor or graft or virus infected cells causing their destruction. In addition when T-cells proliferate in response to antigen they produce lymphokines which participate in regulation of the immune response as well as removal of the foreign antigen. T-cells are directly involved in cell mediated immunity to tumor cells, virus-infected cells and other cellular antigens and clearly help in recovery from such disease processes. Also, the T-cells are responsible for allograft rejection, delayed, cutaneous hypersensitivity (DCH), chemical sensitization to poison ivy, oak, sumac as well as certain metals. This DCH reaction is called such because it takes 24–48 hours to develop subsequent to exposure to the antigen. Cellular immunity to new antigens usually occurs a few days before the primary (IgM) antibody response occurs in mammals and their are memory T-cells which are responsible for long term immunity. Another T-lymphocyte subpopulation is the natural killer (NK) T-cells (large granular lymphocytes) and these cells are called into action without prior antigenic provocation. These NK cells are active against tumors or virus infected cells and they can be stimulated to higher levels of activity (proliferation) by interferon. These cells are said to provide a key role in "immune surveillance" against cancer. T-cells as mentioned above, secrete lymphokines, a diverse and potent array of biologically active molecules with a variety of effects. Some select examples of these T-cell lymphokines include the interleukin 2 (T-cell growth factor), B-cell growth factor, interferon (gamma), and macrophages produce lymphokines (IL-1). These lymphokines serve at least two roles in the immune response, one is the regulation of immunity and the other is actual direct cytotoxicity (destruction) of tumor cells or virus-infected cells.

Immunomodulating agents activate or inhibit the process of lymphocyte proliferation. Normal lymphocyte proliferation is due to various interactions between antigens, macrophages, T- and B-lymphocytes. Additionally, certain B-lymphocytes can be activated by T-lymphocytes while others are independent of the T-lymphocytes and are activated only by antigens directly. Activated T-lymphocytes can cause macrophages to produce a molecule known as interleukin 2(IL-2) which in turn activates T-lymphocytes, which then stimulate other T- and B-lymphocytes. Activated macrophages can produce monokines such as interleukin 1 (IL-1), which induce T-lymphocyte activation. Chemicals, called mitogens can trigger DNA synthesis and mitosis which are signs of activity in T- and B-lymphocytes. Some mitogens affect only one type of lymphocyte while others affect many types. Immunomodulating agents of various kinds and in varying amounts affect the complex interactions between the components of the immune system. The compounds and compositions of this invention act as immune modulators and affect both T- and B-lymphocytes.

The immune system has been linked to some aspects of aging and may be important in protecting against cancer. The system is necessary for the recognition of changing or aging cells, such as worn out red blood cells, and their subsequent destruction, and for this reason is vital to normal body functions. One theory in the case of cancer is that the transformation of cells to the malignant state may occur fairly frequently but these changed cells are recognized as "not self" and destroyed. Some carcinogens may work by depressing the immune response rather than by transforming cells themselves to a malignant state. This would mean that the body would no longer destroy the spontaneously transformed cells and a cancerous growth could escape, resulting in a tumor. Immunostimulation could be useful in treating such cancers.

Some of the methods of treating cancer, surgery, cytotoxic chemotherapy, and radiation for example, can result in a suppression or drastic variation of the normal functions of the immune system. Immunostimulatory drugs, such as the compounds and compositions of this invention can be very effective in combating and/or preventing various infections which can result due to the depressed immune system.

OBJECTS OF THE INVENTION

An object of the invention is to provide novel compounds having immunomodulatory activity.

Another object of the invention is to provide methods for producing such compounds.

Another object of the invention is to provide novel compositions effective in the treatment of immune disorders.

Another object of the invention is to provide novel compounds and compositions useful for the treatment of virus infections in mammals especially infections caused by retroviruses and bunyaviruses.

Other objects, advantages and novel features of the invention will become apparent from the following detailed description.

DESCRIPTION OF THE INVENTION

The compounds of this invention are the presently preferred members of a class of compounds including, for example compounds in which the methylthio group is replaced with a lower alkyl or substituted lower alkyl group; the sulfur atom is oxidized, either partially or fully; or, in fact, the alkyl group is replaced with another functionality such as acyl or substituted acyl group.

The invention will describe MMFBL and MTMFBL. Most of the chemistry employed with the thiomethyl compound is also applicable to the methoxy compound.

MTMFBL is prepared by reaction between ascorbic acid and the novel compound 2-methylthiomethyl-2,5-dimethoxy-2,5-dihydro furan. MMFBL is prepared by the same reaction using the novel 2-methoxymethyl-2,5-dimethoxy-2,5-dihydrofuran.

The reaction is carried out in an aqueous medium at ambient temperatures in the presence of a catalytic amount of a strong inorganic or organic acid, suitably a mineral acid such as sulfuric or a halogen acid, preferably hydrochloric acid. Preferably the reaction is conducted in an inert atmosphere such as nitrogen or helium.

The preferred reaction medium is water, although other solvents may be added, especially water miscible solvents such as lower alkanols, typically methanol or ethanol, cyclic ethers such as tetrahydrofuran, or ketones, particularly acetone.

Reaction is effected at a temperature of from about 20° C. to 45° C. for a period of from about 2 to 48 hours. The reaction period is not critical. It depends principally on the quantities of the reactants. The reaction is readily followed by conventional analytical methods to determine when the reaction is complete, or when continued reaction is not warranted by expected increase in yield. High performance liquid chromatography is a convenient tool.

Generally equimolar quantities of the reactants will be employed. However, it may be desirable to use a molar excess, e.g., up to about a 10% molar excess of one of the reactants to assure as complete a reaction as possible.

As aforesaid, any of a variety of strong acids can be employed to catalyze the reaction. Typically 0.1% to 1.5% by weight of acid based on the total weight of reactants will be employed. In an aqueous medium, hydrochloric acid is preferred since it is readily removed by precipitation as a chloride salt. However, a stronger carboxylic acid such as trichloroacetic acid or trifluoroacetic acid may be used.

The novel intermediate 2-methylthiomethyl-2,5-dimethoxy-2,5-dihydrofuran is prepared by bromination of the known 2-methylthiomethyl furan under anhydrous conditions in methanol in the presence of an alkaline reagent, suitably an alkali metal carbonate or bicarbonate at low temperature, e.g., $-15°$ C. to $-30°$ C. The reaction is preferably carried out in an inert atmosphere, e.g. nitrogen. The time of the reaction is not critical, but is conveniently from about 2 to 6 hours. A reaction inert solvent such as a lower halohydrocarbon may be employed, but is not essential.

The 2-methylthiomethyl furan may be prepared by reaction of furfuryl mercaptan with methyl iodide in the presence of a strong base.

The novel 2-methoxymethyl-2,5-dimethoxy-2,5-dihydrofuran is similarly prepared from the known 2-methoxymethyl furan.

Those skilled in the art will recognize that several stereoisomers of the compounds of this invention may exist. The most obvious are those based on L- and D-ascorbic acid. However, as is known, further isomers of each of these isomers also exist, i.e., the 5-isoascorbic acids. So far as is known all isomers of the compound of the invention have some activity, although certain of them are undoubtedly more active than others as is usually the case with naturally occurring physiologically active substance. As a practical matter, it is normally most convenient to synthesize the compounds of the invention without separation of stereoisomers and to utilize the stereoisomeric mixtures so produced. Applicants herein have followed the conventional practice in the specification and claims, i.e., unless specifically described or claimed the formulas employed include the stereoisomeric modifications.

The ability of the compounds of this invention to stimulate an immune response has been established by a number of art recognized tests.

One of these tests is the lymphocyte blastogenesis assay which measures the ability of the compound under test to affect DNA synthesis and mitosis of T- and B- lymphocytes isolated from mouse spleens.

Mitogens are substances which stimulate DNA synthesis and mitosis. The mitogens used in these studies were phytohemaglutinin (PHA) which is isolated from the red kidney bean and concanavalin-A (Con-A) which is isolated from the jack bean. Con-A binds to specific receptors (glycoproteins) containing mannosyl or glycosyl moieties and stimulates all murine T-cells to synthesize DNA, divide, and release lymphokines. Con-A in a soluble form allows distinction between T- and B-cells in the mouse, because although both T- and B-cells can bind $10^6$ molecules of Con-A per cell, only T-cells are stimulated when this lectin is presented in a soluble form. PHA stimulates only subpopulations, T-2 cells, of T-cells in the mouse. In humans, both T- and B-cells are probably stimulated. The activation of B-cells by PHA may be indirect and mediated by the release of soluble mediators from PHA-activated T-cells.

The lymphocyte blastogenesis test is a method to assess the ability of immunocompetent T- or B-cells to respond to a polyclonal mitogen (i.e., PHA or Con-A) or a specific antigen. It may be performed on lymphocytes obtained from mice treated with immunostimulators in vivo or the entire assay can be performed in vitro. The assay as described below uses minimal doses of polyclonal mitogens to induce blastogenesis (proliferation measured by DNA synthesis), in order to be able to assess the phenomena of amplification. Hence, the procedure is designed to test the ability of potential immunomodulators to restore normal immunologic parameters.

The lymphocyte blastogenesis test is carried out as follows:

1. Sacrifice individual mice/experimental group by cervical dislocation.
2. Immerse mice in a mild disinfectant solution (Povadyne).
3. Remove spleens and place in a sterile 6 well plate containing 5 ml/well of RPMI-1640.
4. Make a single cell suspension by mincing spleens with a sterile toothed forcep.
5. Place cell suspension in a sterile centrifuge tube and allow large clumps to settle for 10 minutes.
6. Remove single cell suspension by pipetting supernatant into another sterile centrifuge tube.
7. Centrifuge cell suspension for 10 mins. at 1100 RPM in GLC-2B.
8. Aseptically remove supernatant and discard.
9. Resuspend cell button in 5 mls of RPMI-1640, and centrifuge. Wash cells in this manner two more times.
10. Resuspend cells in 5 mls of RPMI-1640 containing 10-15% Human AB heat-inactivated (Pel-Freeze, Rogers, AR or BioBee, Boston, Mass.).
11. Perform viable cell count using 0.25% trypan blue exclusion dye made in physiological isotonic saline. Non-viable cells stain blue.
12. Adjust viable cell concentration to $5.0 \times 10-6$ cells/ml in RPMI-1640 containing human AB sera.
13. Aliquot in sextuplicate wells of a 96 well sterile round bottom tissue culture plate with 0.1 ml/well of the various cell suspensions to be tested.
14. Add to above replicate sextuplicate cells 2.5, 5.0 or 7.5 µg/ml of Con A, and to replicate again of 10, 15 or 20 µg/ml of PHA.
15. Include in the experiment a control plate which contains the same cell groups as above, but receive a 0.1 ml of media instead of mitogen.
16. Humidify plate by filling outside wells of plate with media.
17. Incubate plates at 3 C. with 5% CO-2 for 48 hours.
18. After 48 hours all wells receive 0.025 mls of a 0.4 microcurie/ml solution of C-14 methyl thymidine and incubate at 37 C, 5% CO-2 for 18 hours.
19. The cells are harvested using a Brandel M-12 Cell Harvestor (Brandel, Rockville, Md.) onto filter paper discs using phosphate buffered saline at physiological osmolarity. (285-320 mos).
20. The filter paper disks are placed into Packard miniscintillation vials and allowed to dry for 18 hours.
21. Once dried, the vials are filled with 2 mls of a scintillation cocktail containing 4 liters of scintillation grade toluene, 16.0 g of 2,5-diphenyloxazole (PPO) and 0.4 g of 1,4-Bis (2-(5-Phenyloxazoly) benzene (POPOP).

22. The vials are counted in a LKB 1212 Rackbeta (LKB Instruments, Gaithersburg, Md.) Liquid scintillation counter for two minutes/vial.

Table I shows the results of the lymphocyte blastogenesis assay on MTMFBL. It will be noted that the compound gave improved responses compared to the control with both mitogens.

TABLE I

EFFECT OF MTMFBL
ON THE LYMPHOCYTE BLASTOGENESIS ASSAY

| DRUG MG/KG | RPMI | PHA 20.0 UG/ML | % CHANGE | CONA 7.5 UG/ML | % CHANGE |
|---|---|---|---|---|---|
| 0 | 91 +−45 | 534 +−101 | | 749 +−358 | |
| 12.5 | 48 +−16 | 1104* +−78 | +106 | 214# +−74 | −70 |
| 25.0 | 25 +−11 | 110# +−7 | −81 | 5235* +−118 | +598 |
| 50.0 | 38 +−16 | 2096* +−201 | +292 | 4098* +−461 | +447 |
| 100 | 27 +−7 | 853* +−87 | +60 | 6213* +−444 | +729 |
| 200 | 104 +−22 | 3620* +−471 | +557 | 4631* +−448 | +518 |

*SIGNIFICANT INCREASE OVER CONTROLS P < 0.05
SIGNIFICANT INCREASE OVER CONTROLS P < 0.05

RPMI is a semi-synthetic cell growth medium available from (Hazelton Labs, Inc. Denver, Pa.) and comprises all the essential amino acids, vitamins, buffers, and salts required for mammalian cell growth except serum growth factors supplied using an animal (bovine) source.

The Jerne hemolytic plaque assay is an assay procedure which measure the IgM or IgG isotypes of specific antibody produced by antigen used to immunize the mice. The procedure demonstrates antibody production to T-cell dependent antigens by single B-lymphocytes. The direct assay detects IgM and the indirect assay detects IgG-specific antibody.

The procedure is as follows:

Washed spleen cells are added to an agarose (FMC, Rockland, Me.) preparation containing sheep red blood cells (SRBC) and guinea pig complement. A drop of this mixture is transferred to a small petri dish; a cover slip is then placed over the drop to flatten it. The agarose prep is allowed to solidify. Then, the dishes are placed in a small humidified chamber inside a CO-2 incubator overnight.

Small pinpoint cleared areas (plaques) will be observed under the cover slip. The cleared areas are caused by antibody, specific to the SRBC's being released by stimulated spleen cells and in conjunction with the complement, lyse surrounding SRBC's. These plaque forming cells (PFC's) are counted, and calculations are performed to obtain PFC's per $1 \times 10-6$ spleen cells.

| Reagents: | Sheep Red Blood Cells | Guinea Pig Complement |
|---|---|---|
| | Sea Plaque Agarose | 30 mm petri Dishes |
| | RPMI-1640 | 22 × 22 × 1½ cover slips |

Methods

Spleens are harvested from mice according to a standard procedure and adjusted to a final concentration of $1 \times 10^7$ cells/ml in 20% RPMI-1640.

2. SRBC's are adjusted to a final concentration of 50% in RPMI-1640.

3. Reconstitute Guinea Pig Complement (GPC) (Hazelton-Dutchland Inc., Denver, Pa.) by adding several buffered diluent directly to lyophilized GPC. Dilute 1:7 with RPMI-1640 by adding 3 ml of RPMI media to 0.5 ml complement.

4. Prepare Sea Plaque Agarose (FMC, Rockland, Me.) at 0.7% to 25 ml of RPMI-1640, add 0.175 g of the agarose in a 50 ml sterile flask. Place over medium heat, use stirring bar at lowest speed to stir gently. Remove from heat prior to boiling. Place in 37 C water bath immediately.

5. Place all reagents (SRBC's, GPC and spleen cell preps) in water bath for 15 minutes to equilibrate to 37° C.

6. For each preparation to be tested, place a 12×75 mm glass test tube into rack in 37 C water bath. Add 0.7 ml of the agarose to each 12×75 tube.

7. Adjust three separate Rannin pipetman (Gilson, Middleton, Wis.) to 0.05, 0.1, 0.2 ml.

8. To the first 12×75 mm tubes containing agarose, add 0.2 ml of the first spleen cell prep. Next, add 0.05 ml of the complement. Add 0.05 ml of SRBC's Mix very well, until SRBC's are in a uniform suspension.

9. Label the sides of both top and bottom of a petri dish to correspond to the cell group.

10. Using the 0.1 ml pipette, withdraw 0.1 ml of the agarose/cell prep and dispense into center of petri dish-top. Repeat immediately for bottom of petri dish.

11. Carefully place/drop a 22×22 mm cover slip squarely over the droplet. Do not move dishes until agarose settles and solidifies.

12. Repeat steps 6-11 for each of the remaining cell preps.

13. After agarose has solidified, transfer to small plastic humidified chamber. Place in incubator. Allow to incubate overnight at 37 C. Read results the following morning.

14. Count and record the number of hemolytic plaques per plate. Average plaque counts between the duplicate sets. Multiply the average number of plaques per group by 2.5 to obtain the number of plaque forming cells per million spleen cells.

Table II records the results of the Jerne assay on the MTMFBL. The compound showed improvement over the control at all levels tested.

TABLE II

EVALUATION OF MTMFBL ON JERNE ASSAY

| GROUP | TMFBL PFC/10$^6$ CELLS | % INCREASE |
|---|---|---|
| Vehicle Control | 6.25 | — |
| SRBC Control | 17.50 | — |
| 200.0 mg/kg | 27.5 | 57 |
| 100.0 mg/kg | 20.0 | 14 |
| 50.0 mg/kg | 53.75 | 207 |
| 25.0 mg/kg | 68.75 | 292 |
| 12.5 mg/kg | 42.50 | 142 |
| 6.2 mg/kg | 21.25 | 21 |

Tables III and IV record the results of additional lymphocyte blastogenesis assays for MTMFBL and MMFBL respectively. The results clearly indicate the significant improvement of the immune response compared to controls at doses of 1 to 10 mg/kg for all nitrogens tested.

Tables V and VI record the results of additional Jerne assays on MTMFBL and MMFBL respectively.

The results clearly indicate that both compounds significantly improved the antigen specific immune response at doses of 1 to 10 mg/kg when compared to the controls.

course, be aware that with these types tests the comparisons must be made within each test group and not between tests.

The ability of the compounds of this invention to

TABLE III

EFFECT OF MTMFBL ON THE LYMPHOCYTE BLASTOGENESIS ASSAY

| DRUG(1) MG/KG | RPMI CONTROL | PHA MITOGEN | P VALUE(2) | CON-A MITOGEN | P VALUE | POKEWEED MITOGEN | P VALUE |
|---|---|---|---|---|---|---|---|
| 0 | 225 | 3729 | — | 6192 | — | 867 | — |
|   | ±79 | ±884 |   | ±962 |   | ±175 |   |
| 1 | 196 | 6790 |   | 13,146 |   | 3038 |   |
|   | ±73 | ±1074 | <.0005 | ±1657 | <.0005 | ±827 | <.0005 |
| 10 | 202 | 5634 |   | 10,288 |   | 2437 |   |
|   | ±90 | ±1020 | ≧.0005 | ±753 | <.0005 | ±688 | <.0005 |
| 100 | 206 | 4512 |   | 7388 |   | 1417 |   |
|   | ±128 | ±1009 | n.s. | ±1745 | n.s. | ±373 | ≧.0005 |

(1)Drug was administered daily for four (4) days via the intraperitoneal (i.p.) route. Mice were sacrificed on the fifth day and processed individually. Spleens were removed, lymphocytes isolated and the assay performed. There were nine (9) mice per test group.
(2)Student's T-test for paired data; Drug treated group compared to zero (0) drug control group in each mitogen test system.
(3)Mice = C57BL/6, N = 9

TABLE IV

EFFECT OF MTMFBL ON THE LYMPHOCYTE BLASTOGENESIS ASSAY

| DRUG(1) MG/KG | RPMI CONTROL | PHA MITOGEN | P VALUE(2) | CON-A MITOGEN | P VALUE | POKEWEED MITOGEN | P VALUE |
|---|---|---|---|---|---|---|---|
| 0 | 71 | 3745 | — | 7336 | — | 1385 | — |
|   | ±25 | ±456 |   | ±633 |   | ±250 |   |
| 1 | 96 | 4479 |   | 10,022 |   | 2094 |   |
|   | ±30 | ±700 | ≧.01 | ±1706 | <.0005 | ±514 | ≧.0005 |
| 10 | 139 | 4561 |   | 9701 |   | 1956 |   |
|   | ±41 | ±1047 | >.01 | ±1336 | >.0005 | ±858 | ≧.025 |
| 100 | 142 | 3566 |   | 6431 |   | 1441 |   |
|   | ±63 | ±978 | n.s. | ±2494 | n.s. | ±389 | n.s. |

(1)Drug was administered daily for four (4) consecutive days via the i.p. route. Mice were sacrificed on the fifth day and processed individually. Spleens were removed, lymphocytes isolated and the assay performed. There were nine (9) mice per test group.
(2)Student t-test for paired data; Drug treated group compared to zero (0) drug control group in each mitogen test system.
(3)Mice = C57BL/6, N = 9

TABLE V

EVALUATION OF MTMFBL ON THE JERNE ASSAY

| GROUP | PFC/$10^6$ CELLS | % INCREASE | P VALUE* |
|---|---|---|---|
| SRBC Control | 214 ± 111 | — | — |
| 100 mg/kg | 273 ± 150 | 22% | n.s. |
| 10 mg/kg | 395 ± 153 | 46% | ≧.005 |
| 1 mg/kg | 485 ± 194 | 56% | ≧.0005 |

Mice = C57BL/6, N = 9
Dose = i.p. daily for four days.
SRBC = 2% solution in saline given i.p. on day zero.
Harvest/Assay = Day 7
*Student's t-test for paired data; comparison of drug treated group to SRBC control.

TABLE VI

EVALUATION OF MTMFBL ON THE JERNE ASSAY

| GROUP | PFC/$10^6$ CELLS | % INCREASE | P VALUE* |
|---|---|---|---|
| SRBC Control | 237 ± 108 | — | — |
| 100 mg/kg | 375 ± 134 | 37% | ≧.025 |
| 10 mg/kg | 393 ± 144 | 40% | >.01 |
| 1 mg/kg | 241 ± 83 | 2% | n.s. |

Mice = C57BL/6, N = 9
Dose = i.p. daily for four days.
SRBC = 2% solution in saline given i.p. on day zero.
Harvest/Assay = Day 7
*Student's t-test for paired data; comparison of drug treated group to SRBC control.

The tests reported in Tables III through VI are based upon tests conducted with a larger number of animals and a broader spectrum of mitogens than those reported in Tables I and II. They support and amplify the original conclusions based upon the tables.

It will be apparent that the absolute values of numbers recorded in the separate tables differ appreciably amongst themselves. Whose skilled in the art will, of course, be aware that with these types tests the comparisons must be made within each test group and not between tests.

inhibit the immune response has been established by a delayed type hypersensitivity test (DHT) which is art recognized as a measure of suppression of the immune system. The oxazolone mouse ear swelling test is an acute model for contact delayed cutaneous hypersensitivity (Evans et al, Brit. J. Pharmacol. 43:403-408, 1971; Carey et al., Agents and Actions 29:65-67, 1990).

In the DHT test, mice were immunized to the chemical 4-ethoxymethylene-2-phenyl-oxazol-5-one (oxazolone) by single or multiple applications of 100 µl of a 3% (30 mg/ml) solution in acetone. Ten to 14 days later, the immunized mice were challenged by the application of a 1% solution of oxazolone in acetone to the outer surface of the ear 60 min. after administration of compounds of this invention. Control animals were challenged with acetone only.

The immune response of the animals to oxazolone was measured as swelling of the ear as measured by increase in ear thickness measured with a caliper.

Down regulation of the DHT immune response was measured as a decrease in swelling of the challenged ear after treatment of the mice with test drug.

Percent inhibition of the DHT response is calculated as follows:

$$= \frac{(Oc - Vc) - (OT - Vc)}{(Oc - Vc)} \times 100$$

wherein:
Oc=Oxazolone control
Vc=Vehicle control
Ox=Oxazolone challenged, drug treated The results of several tests with mice at various dosage levels are shown in Table VII. Note that a significant percent decrease in ear swelling (DHT) was produced at all doses of both MTMFBL and MMFBL tested. Optimum inhibition of the DHT reaction is produced at doses of the compounds which are greater than 100 mg/kg.

TABLE VII

|  |  |  | Ear Swelling (ETU)* | | | |
|---|---|---|---|---|---|---|
| DRUG | DOSE mg/kg | OX Challenge | 8 Hours | % INHIBITION | 24 Hours | % INHIBITION |
| NONE | — | — | 25.0 ± 2.0 |  | 25.0 ± 2.0 |  |
| NONE | — | + | 40.0 ± 7.1 |  | 47.5 ± 3.5 |  |
| MMFBL | 400 | + | 26.7 ± 2.9 | (89) | 30.0 ± 2.0 | (78) |
| MMFBL | 200 | + | 28.3 ± 2.9 | (78) | 31.7 ± 2.9 | (70) |
| MMFBL | 100 | + | 30.0 ± 2.0 | (67) | 33.3 ± 2.9 | (63) |
| MTMFBL | 400 | + | 27.5 ± 2.9 | (84) | 31.3 ± 2.5 | (72) |
| MTMFBL | 200 | + | 28.8 ± 4.3 | (75) | 32.5 ± 2.9 | (67) |
| MTMFBL | 100 | + | 32.5 ± 2.9 | (50) | 33.8 ± 2.5 | (61) |

*ETU = EAR Thickness Unit; 1 unit = 0.01 mm

The biologically active compounds of this invention may be administered in effective amounts, alone or in combination with acceptable pharmaceutical carriers, the choice of which is determined by the preferred route of administration, the solubility of the compound, the effect desired and standard pharmaceutical practice The oral and parenteral dosage units will be prepared in accordance with standard procedures and will contain the selected active compound as the only or principal active ingredient in the composition. Any of a wide variety of known inert excipients may be employed to prepare compositions useful in the practice of this invention. These include, for example, dextrose, starch, talc, various types of clay, mineral oil, cottonseed or sesame oil, as well as water or various miscible and immiscible aqueous compositions in which the therapeutic agent is soluble or may be suspended with the aid of known surfactants.

For buccal and sublingual administration the active ingredient can be formulated in tablet form with water soluble binding agents such as lactose or other palatable carbohydrates.

For rectal administration suppositories or inserts containing the active ingredient dispersed in such reagents as cocoa butter, petrolatum, or other natural lubricants or in a synthetic emmolient such as polyethylene glycol 1000 or polyethylene glycol 4000 may be used.

It is convenient to administer the active agents of this invention from sustained release dosage forms. This avoids the necessity of constant clock watching or interruption of normal daily activities. A number of compositions suitable for such preparations are known and can be usefully employed.

For oral administration, the selected therapeutic agent may be in a time disintegrating tablet or pellet coated with various thickness of known materials such as carnauba wax, cellulose esters and ethers, fats, keratin, gluten or various natural or synthetic esters. Tablets in which the selected agent is contained in a slowly dissolving core such as a core of stearic acid or castor oils are useful. Mixed release granule tablets comprising mixtures of the drug itself and the drug in separate particles coated with materials which dissolve at different rates such as dehydrogenated castor oil or fatty acids can also be employed. Alternatively the active material can be bound to an ion exchange resin such as a sulfuric acid type cation exchange resin.

A number of transdermal formulations are possible for use in the practice of this invention. They are discrete dosage forms in construction systems which, when applied to the skin deliver the therapeutic agent through the skin at a controlled rate for systemic circulation. The system typically comprises an outer covering barrier, a drug reservoir which may have a rate of release controlling membrane, a contact adhesive applied to some or parts of the system at the system/skin interface and a protective layer which is removed before applying the system.

The drug reservoir is normally some type of polymer matrix such as a polyvinylpyrrolidone or a silicone polymer from which the drug is slowly released. A microporous membrane such as a polypropylene film may serve as a membrane to control the rate of release.

For intra-articular injection aqueous suspensions may be employed. In this case various suspending and wetting agents may be added to the composition to obtain a suspension not tending to settle out easily or to pack down in the bottle in which it is stored. Intramuscular and subcutaneous dosage forms may be prepared by standard pharmaceutical practice.

The compounds may be used in association with other therapeutic agents including, for example, antibiotics or antiviral agents. It may also be useful to employ the compounds in association with natural immunostimulators such as interleukin 1 and 2, or interferon or it's synthetic inducers (i.e. poly IC-LC etc.), B-cell growth factors, or tumor necrosis factor. They may be administered by any of the usual routes of administration including intramuscular or intraveneous.

The physician or veterinarian in attendance will determine the optimum dosage in consideration of such factors as age, weight and general health of the subject. A dose which will be effective for immunostimulation will normally be from about 1 to 100 mg/kg body weight. For suppression, an effective range is typically 200 to 600 mg/kg b.w. The dosage may be administered in one treatment, several treatments given over a period of time, or over an extended period of time in transdermal and other sustained release preparations.

The compositions of the invention may be made available in dosage unit forms containing a therapeutically effective amount of active ingredient per dosage unit.

The following examples are given solely for the purpose of illustration and are not to be construed as limitations of this invention, many apparent variations of which are possible without departing from the spirit or scope thereof.

EXAMPLE 1

Preparation of MTMFBL

Preparation of 2-methylthiomethyl furan

Finely powdered potassium hydroxide (19.97 g, 0.355 mole) was added portionwise to a cold mixture of furfuryl mercaptan (40.0 g, 0.350 mole) and iodomethane (49.72 g, 0.350 mole). The reaction mixture was allowed to stir for 6 hours and 36 mL of water were added. The solution was extracted with ether ($3 \times 300$ mL) and the combined organic fractions were dried over anhydrous sodium carbonate. After the removal of the solvent, the residue was distilled under reduced pressure to give 15.0 g (34%) colorless product, bp 61° C. (20 mm Hg), $n_D = 1.5210$.

Preparation of 2-methylthiomethyl-2,5-dimethoxy-2,5-dihydro furan

A mixture of 2-methylthiomethyl furan (23.3 g, 0.182 mole), anhydrous sodium carbonate (32.16 g, 0.303 mole), methylene chloride (40 mL) and absolute methanol (40 mL) was cooled to $-20°$ C. under nitrogen atmosphere. A solution of bromine (24.32 g, 0.152 mole) in 60 mL absolute methanol was added over a period of one hour. The reaction mixture was stirred for another 4 hours and filtered by suction. The filtrate was stirred with anhydrous potassium carbonate (10 g—1 hour) and filtered. The solvents were removed on the rotatory evaporator and methylene chloride (100 mL) was added. The organic solution was dried over anhydrous sodium sulfate, filtered and the solvent was removed on the rotatory evaporator. The residue was distilled under reduced pressure to give 16.51 g (57%) of pure product, bp 66°–68° C. (0.4 mm Hg), $n_D = 1.4860$.

Preparation of 2-(5-methylthiomethyl-2-furyl)-2-hydroxy-3-keto-4-dihydroxyethyl-butyrolactone (MTMFBL)

L-Ascorbic acid (8.8 g, 0.05 mole) was dissolved in 62 mL water that had been purged with nitrogen for 1 hour. Freshly distilled 2-methylthiomethyl-2,5-dimethoxy-2,5-dihydrofuran (9.5 g, 0.05 mole) was added dropwise with stirring over a period of 1 hour. The reaction mixture was not completely homogeneous. Twenty four hours after the addition of the dihydrofuran, the insoluble droplets were removed by treatment with methylene chloride. The aqueous fraction was frozen and freeze-dried to give 14.2 g (98%) crude product. The amorphous solid was dissolved in 100 mL ethyl acetate and was shaken with 3 g decolorizing charcoal and 3 g celite. After filtration, the solvent was removed under vacuum to give 12.7 g (88%) amorphous product, sinters 40°–42° C.

EXAMPLE 2

Preparation of MMFBL

Preparation of 2-methoxymethyl furan

Furfuryl alcohol (225 mL, 2.6 mole) and iodomethane (162 mL, 2.6 mole) were placed in a 1 L three-necked flask equipped with a mechanical stirrer and a reflux condenser. To the cold ($-10°$ C.) mixture was added in small portions powdered potassium hydroxide (148 g, 2.6 mole). After the addition of KOH, the reaction mixture was stirred for 6 hours at ambient temperature. Cold water (200 mL) was added and the organic fraction was extracted with ether ($3 \times 300$ mL). The ether extract was dried (anhydrous $Na_2SO_4$) and the solvent evaporated. Distillation of the crude product gave 193 g (66%) of the desired compound (bp 130°–134°) as a colorless liquid.

Preparation of 2-methoxymethyl-2,5-dimethoxy-2,5-dihydrofuran

2-Methoxymethyl furan (120.4 g, 1.07 moles), anhydrous methanol (250 ml, 6.18 moles), anhydrous sodium carbonate (190 g), and methylene chloride (250 ml) were placed in a 3L three-necked flask equipped with a mechanical stirrer and an addition funnel. The mixture was cooled to $-10$ to $-15°$ C. and an ice-cold solution of bromine (53 ml, 1.04 moles) in 500 ml anhydrous methanol was added dropwise with stirring. Four hours after the addition of the bromine solution, the mixture was filtered by suction. The excess solvent was removed on a rotatory evaporator and the crude product was distilled under reduced pressure to give colorless 2-methoxymethyl-2,5-dimethoxy-2,5dihydrofuran (118.3 g, 65%), bp. 57°–58° C. (0.2 mm Hg), $n_D = 1.4414$.

Preparation of 2-(methoxymethyl-2-furyl)-2-hydroxy-3-keto-4-dihydroxyethylbutyrolactone (MMFBL)

Distilled water (375 mL) was degassed for 1.5 hours in a three-necked 1 L flask equipped with a magnetic stirring bar. L-Ascorbic acid (75.0 g) was added and to the resulting solution was added 2-methoxymethyl-2,5-dimethoxy-2,5-dihydrofuran (74.9 g) dropwise with stirring over a period of 1 hour. Four hours after the end of the addition, the reaction mixture was frozen and partially evacuated on a Virtis Freezemobile. Sixty-five hours later, the liquefied reaction mixture was again frozen and freeze-dried at 10–15 millitorr for at least one week to give the desired product (117.84 g).

EXAMPLE 3

Tablet Formulation

|  | Mg/tablet |
|---|---|
| Formula: | |
| MTMFBL | 200.00 |
| Citric acid | 1.00 |
| Lactose | 33.00 |
| Diacalcium phosphate | 70.00 |
| Pluronic, F-68 | 30.00 |
| Sodium Lauryl Sulfate | 15.00 |
| Polyvinylpyrrolidone | 15.00 |
| Carbowax 1500 | 5.00 |
| 3A alcohol 50 ml./1000 tablets | |
| Corn Starch | 30.00 |
| Dry: | |
| Sodium Lauryl Sulfate | 3.00 |
| Magnesium stearate | 3.00 |
| TOTAL WEIGHT | 350.00 |

Procedure—Mix together the MTMFBL, citric acid, Pluronic F-68, sodium lauryl sulfate, lactose and diacalcium phosphate. Screen through No. 60 mesh screen. Granulate the screened mix with an alsoholic solution containing the polyvinylpyrrolidone, Carbowas 1500 and 6000. Add additional alcohol, if necessary, to bring powder mix to a pasty mass. Add corn starch and continue mixing until uniform damp granules are formed. Pass the damp granulation through a No. 10 screen and dry in an oven at 100° C. for about 4 hours. Screen the dried granulation using a No. 16 screen, add sodium lauryl sulfate and magnesium stearate, mix and compress on a tablet machine to specifications.

Similar tablets are prepared with MMFBL.

EXAMPLE 4

Capsule Formulation

| Formula: | Mg./capsule |
| --- | --- |
| MTMFBL | 100.00 |
| Citric acid | 1.00 |
| Pluronic F-68 | 40.00 |
| Sodium lauryl sulfate | 20.00 |
| Lactose | 238.00 |
| Magnesium stearate | 1.00 |

Procedure—Mix together the MTMFBL, citric acid, Pluronic F-68, sodium lauryl sulfate and lactose. Pass through a No. 80 screen. Add the magnesium stearate, mix and encapsulate into the proper size 2-piece gelatin capsule.

Similar capsules are prepared with MMFBL. cl EXAMPLE 5

Parenteral Formulation

| Formula: | | |
| --- | --- | --- |
| MTMFBL B | mg/10 ml | 200 |
| Benzyl alcohol, UF | mg/10 ml | 50.0 |
| Methyl paraben, USP | mg/10 ml | 18.0 |
| Propyl paraben, USP | mg/10 ml | 2.0 |
| Water | ml | 10 |

Procedure—Dissolve the parabens in approximately 8.5 ml of water at 60° to 70° C. Cool the solution to 40° C. and add the benzyl alcohol. Cool the resultant solution to room temperature and add the MTMFBL. Place the suspension in a sterile receptacle. Fill suitably sized vials cap loosley and autoclave for one-half hour at 110° C. (15 p.s.i.g.). Each milliliter of this formulation delivers 20 mgs. of active compound.

Parenteral formulations containing MMFBL are similarly prepared.

What is claimed is:

1. 2-(5-methylthiomethyl-2-furyl)-2-hydroxy-3-keto-4-dihydroxyethylbutyrolactone represented by the formula:

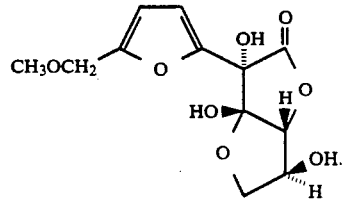

2. 2-(5-methoxymethyl-2-furyl)-2-hydroxy-3-keto-4-dihydroxyethylbutyrolactone represented by the formula:

3. A pharmaceutical composition useful for immunosuppression in mammals containing a pharmaceutically acceptable carrier together with a therapeutically effective amount of 2-(5-methylthiomethyl-2-furyl)-2-hydroxy-3-keto-4-dihydroxyethylbutyrolactone.

4. A pharmaceutical composition in dosage unit form useful for immunosuppression in mammals containing a therapeutically effective amount of 2-(5-methylthiomethyl-2-furyl)-2-hydroxy-3-keto-4-dihydroxyethylbutyrolactone together with a pharmaceutically acceptable carrier.

5. A pharmaceutical composition useful for immunosuppression in mammals containing a pharmaceutically acceptable carrier together with a therapeutically effective amount of 2-(5-methoxymethyl-2-furyl)-2-hydroxy-3-keto-4-dihydroxyethylbutyrolactone.

6. A pharmaceutical composition in dosage unit form useful for immunosuppression in mammals containing a therapeutically effective amount of 2-(5-methoxymethyl-2-furyl)-2-hydroxy-3-keto-4-dihydroxyethylbutyrolactone together with a pharmaceutically acceptable carrier.

7. A method of inhibiting the immune response of a mammal in need of such inhibition which comprises administering an amount which is effective to effect such inhibition of 2-(5-methylthiomethyl-2-furyl)-2-hydroxy-3-keto-4-dihydroxyethylbutyrolactone.

8. The method of claim 7 wherein the mammal is a human.

9. The method of claim 7 wherein the mammal is an animal.

10. A method of inhibiting the immune response of a mammal in need of such inhibition which comprises administering an amount which is effective to effect such inhibition of 2-(5-methoxymethyl-2-furyl)-2-hydroxy-3-keto-4-dihydroxyethylbutyrolactone.

11. The method of claim 10 wherein the mammal is a human.

12. The method of claim 10 wherein the mammal is an animal

* * * * *